(12) United States Patent
Hall et al.

(10) Patent No.: US 11,311,156 B2
(45) Date of Patent: Apr. 26, 2022

(54) INSTRUMENTED TOILET SEAT

(71) Applicant: Hall Labs LLC, Provo, UT (US)

(72) Inventors: David R. Hall, Provo, UT (US); Dan Allen, Springville, UT (US); Andrew Davis, Provo, UT (US); Justin R. Robinson, Provo, UT (US)

(73) Assignee: Medic, Inc., Provo, UT (US)

( * ) Notice: Subject to any disclaimer, the term of this patent is extended or adjusted under 35 U.S.C. 154(b) by 0 days.

(21) Appl. No.: 16/591,488

(22) Filed: Oct. 2, 2019

(65) Prior Publication Data

US 2020/0029756 A1 Jan. 30, 2020

Related U.S. Application Data (63) Continuation of application No. 15/277,265, filed on Sep. 27, 2016, now abandoned.

(51) Int. Cl.
*A47K 13/24* (2006.01)
*A47K 17/02* (2006.01)
*A47K 13/30* (2006.01)
*A61B 5/0205* (2006.01)
*A61B 5/00* (2006.01)
*G16H 40/63* (2018.01)
*G16H 10/60* (2018.01)

(52) U.S. Cl.
CPC ............ *A47K 13/24* (2013.01); *A47K 13/302* (2013.01); *A47K 17/02* (2013.01); *A61B 5/0205* (2013.01); *A61B 5/6891* (2013.01); *G16H 40/63* (2018.01); *G16H 10/60* (2018.01)

(58) Field of Classification Search
CPC ...... A47K 13/00; A47K 13/10; A47K 13/105; A47K 13/30; A47K 17/02; A47K 17/026; A61B 5/6887–6889; A61B 5/6891; A61B 5/6894; A61B 8/0875; A61B 8/40; A61B 8/42–429; A61B 8/46; A61B 8/469
USPC ................. 4/237, 246.1, 254, 443–448, 661; 600/300, 437–442; 702/131, 19
See application file for complete search history.

(56) References Cited

U.S. PATENT DOCUMENTS

| 5,184,359 A * | 2/1993 | Tsukamura ........ A61B 5/02241 4/314 |
| 5,735,798 A * | 4/1998 | Shinohara ............... A61B 5/022 4/314 |
| 2005/0096554 A1* | 5/2005 | Dudik .................. A61B 5/6806 600/500 |
| 2007/0208241 A1* | 9/2007 | Drucker ............... A61B 5/1455 600/323 |
| 2011/0051125 A1* | 3/2011 | Kim .................... A61B 5/14507 356/51 |
| 2016/0374619 A1* | 12/2016 | Borkholder .......... A61B 5/1102 600/301 |

* cited by examiner

*Primary Examiner* — David P Angwin
*Assistant Examiner* — Nicholas A Ros (57) ABSTRACT

A toilet seat with handles is disclosed. The handles include light transmitters and light receivers. The light transmitters and receivers may be used to determine blood oxygen saturation levels and heart rate of a toilet seat user. Ultrasonic transmitters and receivers in the toilet seat handle are also disclosed for determining bone density of a toilet seat user. The handles may be retractable and may include UV sanitation.

18 Claims, 10 Drawing Sheets

INSTRUMENTED TOILET SEAT

CROSS-REFERENCE TO RELATED APPLICATION

This application is a continuation application of U.S. patent application Ser. No. 15/277,265, filed Sep. 27, 2016 and entitled Instrumented Toilet Seat.

TECHNICAL FIELD

The present invention relates generally to using handles in toilet seats for medical purposes. More particularly, the present invention relates to assessment by means of instruments within a toilet seat.

BACKGROUND

Assessment of a person's functional ability, physical health, cognition, and mental health is usually initiated when a physician identifies a potential problem. Specific elements of physical health that may be evaluated include nutrition, vision, hearing, fecal and urinary continence, and balance. Assessment aids in diagnosis of medical conditions, development of treatment and follow-up plans, coordination of management of care, and evaluation of any long-term care needs.

One problem with assessment is that it can take time, requiring a person's time and the time of his or her physician. Another problem with assessments is that, because of demands of a busy clinical practice, many assessments tend to be less comprehensive and more problem-directed. Assessment can also be inconvenient for a person being assessed and/or for his or her physician as one or both may need to travel for the assessment. Additionally, assessments may be often not as frequent or as regular as would be desired to obtain more comprehensive data, due to the above mentioned problems.

SUMMARY OF THE INVENTION

An apparatus is disclosed that overcomes or improves upon the limitations discussed above. In general, the apparatus includes a toilet seat with handles and light transmitters and light receivers. The toilet seat is positioned on a toilet, and the handles may be attached to the toilet seat such that a user can use them to lower and/or raise himself or herself onto/from the toilet seat. The light transmitters and receivers may be then used to determine blood oxygen saturation levels of the user, heart rate of the user, etc. The handles serve multiple purposes such as allowing a user to raise and lower himself or herself from a toilet and the handles provide a health monitoring function of determining blood oxygen saturation level, heart rate, diastolic pressure, and systolic pressure. Handles used to raise and lower individuals do not currently preform the above medical monitoring functions.

In one embodiment, an apparatus is disclosed which includes a toilet seat. The toilet seat includes handles. The handles may include light transmitters and light receivers.

BRIEF DESCRIPTION OF THE DRAWINGS

A more particular description of the invention briefly described above is made below by reference to specific embodiments. Several embodiments may be depicted in drawings included with this application, in which.

DETAILED DESCRIPTION

A detailed description of the claimed invention is provided below by example, with reference to embodiments in the appended figures. Those of skill in the art will recognize that the components of the invention as described by example in the figures below could be arranged and designed in a wide variety of different configurations. Thus, the detailed description of the embodiments in the figures is merely representative of embodiments of the invention, and is not intended to limit the scope of the invention as claimed.

In some instances, features represented by numerical values, such as dimensions, mass, quantities, and other properties that can be represented numerically, may be stated as approximations. Unless otherwise stated, an approximate value means "correct to within 50% of the stated value." Thus, a length of approximately 1 inch should be read "1 inch+/−0.5 inch."

Aspects of the present invention may be described herein with reference to flowchart illustrations and/or block diagrams of methods, apparatus (systems), and computer program products according to embodiments of the invention. Those of skill in the art will understand that each block of the flowchart illustrations and/or block diagrams, and combinations of blocks in the flowchart illustrations and/or block diagrams, may be implemented by computer readable program instructions. Additionally, those of skill in the art will recognize that the system blocks and method flowcharts, though depicted in a certain order, may be organized in a different order and/or configuration without departing from the substance of the claimed invention.

Figure 1:
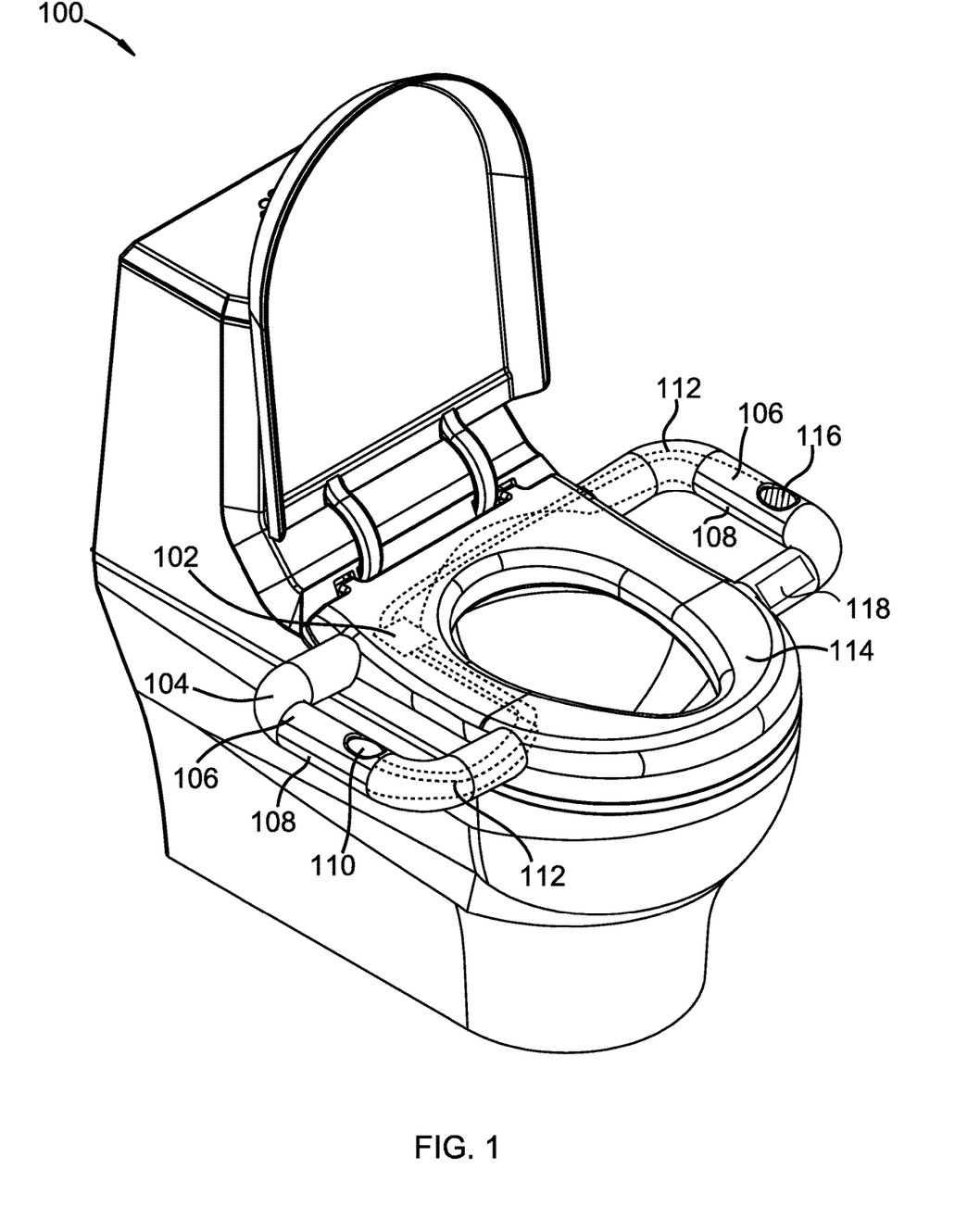
FIG. 1 depicts an apparatus with a toilet seat having a handle.

FIG. 1 depicts an apparatus with a toilet seat having a handle. Apparatus 100 includes toilet seat 114. Toilet seat 114 includes handle 104. Handle 104 includes one or more light transmitters 110 and light receivers 510 (see FIG. 5). Light transmitters 110 and light receivers 510 may use photoplethysmography (PPG) to determine blood oxygen saturation level, heart rate, diastolic pressure, and systolic pressure. PPG detects change in tissue color. Blood absorbs light, so if more blood is in tissue, then less light can transmit through it.

Figure 5:
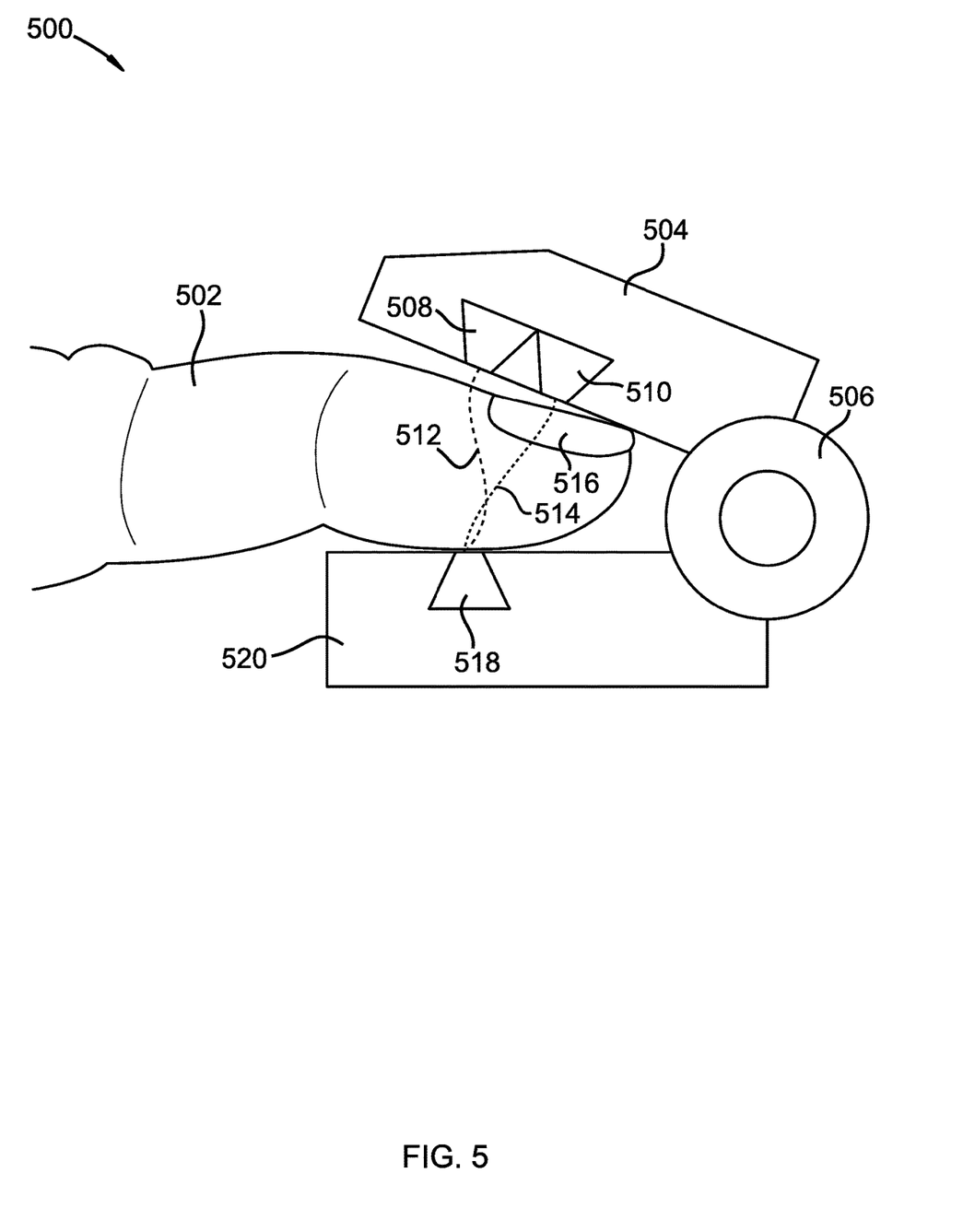
FIG. 5 depicts a side view of a photoplethysmographical device.

In some embodiments, a transmission PPG sensing operation is utilized. In these embodiments, light transmitters 110 emit light at wavelengths between visible and infrared spectrums. Light transmitters 110 may be positioned on one side of a finger and light receivers 510 may be positioned on an opposite side of the finger. When arterial blood flows into the finger, the finger fills with blood. With each heartbeat, light transmission through the finger to light receivers 510 drops. When the blood is oxygenated, absorption specific to oxy-hemoglobin is relatively high. When blood is deoxygenated, absorption specific to deoxy-hemoglobin is high. A relation between changing amplitudes of light transmission with each heart beat is used to estimate blood oxygen saturation level. Heart rate is also estimated by observing the periodicity in the light transmission at a single color, or averaged over many colors. Transmission measurements may use infrared (IR) light to get better transmission through tissue. In some further embodiments, light transmitters 110 may be light emitting diodes (LEDs), white light generators, halogen lights, and/or lasers. The light receivers 510 may be photodiodes or capacitive coupled displays (CCDs). In other embodiment a first handle houses one or more sensors which interface with a hand of a user of the toilet seat while the user is sitting on a toilet. A second handle may be used to house one or more sensors. The sensors in the first and second handles may include electrodes for measuring bio-impedance and temperature of a user of a toilet. The sensors may also include light transmitters and light receivers for determining blood oxygen saturation level, heart rate, diastolic pressure, and systolic pressure. Other sensors may include ultrasonic transmitters and receivers for determining bone density, blood flow, and tissue characteristics of a toilet user. Other sensors may include force sensors such as strain gages for determining a grip strength of a toilet user. Other sensors 610 (see FIG. 6) such as capacitive sensors, resistive sensors, inductive sensors and pressure sensors may be utilized to wake up controller 102 and display 118 when a user contacts handles 104. The first and/or the second handles may retract and extend into and from a side surface of the toilet seat. UV sanitation may be employed to sanitize the handles while the handles are in a retracted state.

In some embodiments, a reflection PPG sensing operation is utilized. In these embodiments, light transmitters 110 may be positioned on one side of a finger and light receivers 510 may be positioned on the same side of the finger. In this arrangement, the light transmitters 110 emit light which transmits through one or more top surfaces of tissue and reflects off a lower layer to return to light receivers 510. Perfusion in capillaries near a surface of skin changes with each heartbeat with phase inverted to transmission PPG sensing. To avoid deep penetration typical of IR wavelengths, which would make a light transmission signal sensitive to arterial behavior and thus reduce the signal resolution due to partial cancellation of an opposing capillary and arterial signals, shorter wavelengths may be desirable. For example, in some further embodiments, light emitted from light transmitters 110 is blue, green, yellow, and/or red.

Blood pressure changes cyclically with each heartbeat. A high pressure point is systolic pressure and a low pressure point is diastolic pressure. When arteries are inelastic, a heart has to push harder to move a same volume of blood, so a resulting pressure in blood vessels increases. A heart beat causes a pressure wave that propagates from heart to body. A pressure is strongest near the heart and is more easily observed in arteries lying close to a surface.

Blood pressure is related to pulse wave velocity (PWV). PWV is related to pulse transit time (PTT) such that PWV=distance/PTT. A PPG signal measured, for example, on a finger is delayed relative to a time difference between PPG signals at locations at different distances from a heart. In some embodiments, handle 104 has two light transmitters 110 and two light receivers 510. A pulse wave is identified at a first time by a first set of a light transmitter 110 and a light receiver 510 at one position on handle 104. The same pulse wave is identified at a second time by a second set of a light transmitter 110 and a light receiver 510 at a different position on handle 104. Due to a change in time between time the first and the second pulse times, PTT is determined. Additionally, due to a difference of distance between the locations of the body where the sets of light transmitters 110 and light receivers 510 were located, PWV can be calculated. Subsequently, blood pressure can be estimated from PTT and PWV.

In some embodiments, apparatus 100 includes two handles 104, each having multiple lights transmitters 110 and multiple light receivers 510. A first set of light transmitters 110 and light receivers 510 may be positioned on one of handles 104. A second set of light transmitters 110 and light receivers 510 may be positioned on another of handles 104. Blood pressure is then estimated using PTT of a pulse between the two handles. This will need to be calibrated for each user, as distances will be different for each.

In some embodiments, light transmitters 110 and light receivers 510 may be positioned under a transparent surface. In other embodiments, light transmitters 110 may be positioned geometrically normal to a face of handle 104. In yet other embodiments, handle 104 includes a cavity covered by transparent material. Light transmitters 110 may be positioned inside the cavity facing the transparent material.

In some embodiments, handle 104 includes a lenticular lens 116 behind which light transmitters 110 and/or light receivers 510 may be placed.

In some embodiments, handle 104 includes a lenticular lens 116 behind which light transmitters 110 and/or light receivers 111 may be placed.

In some embodiments, toilet seat 114 includes two handles 104. Each of handles 104 includes one or more light transmitters and one or more light receivers. In a further embodiment, toilet seat 114 includes more than two handles.

In some embodiments, handle 104 includes a first bioimpedance electrode 106 and a second bioimpedance electrode 108. In a further embodiment, apparatus 100 includes two handles 104, each including a single bioimpedance electrode. In yet further embodiments, handle 104 includes more than two bioimpedance electrodes.

In some embodiments, toilet seat 114 includes controller 102. In these embodiments, toilet seat 114 includes wiring 112 which couples controller 102 to any bioimpedance electrodes, light transmitters, and light receivers.

In some embodiments, handle 104 includes ultrasonic transmitters and ultrasonic receivers. The ultrasonic transmitters send sound waves with frequencies from 20 kilohertz (kHz) up to several gigahertz. These transmitters and receivers may be used to estimate bone mineral density. The transmitters emit sound waves into a part of a user's hand, the receivers collect the sound waves leaving the user's hand, and controller 102 calculates how fast the sound waves pass through the user's hand. From this, controller 102 calculates a bone mineral density of the user.

Figure 3:
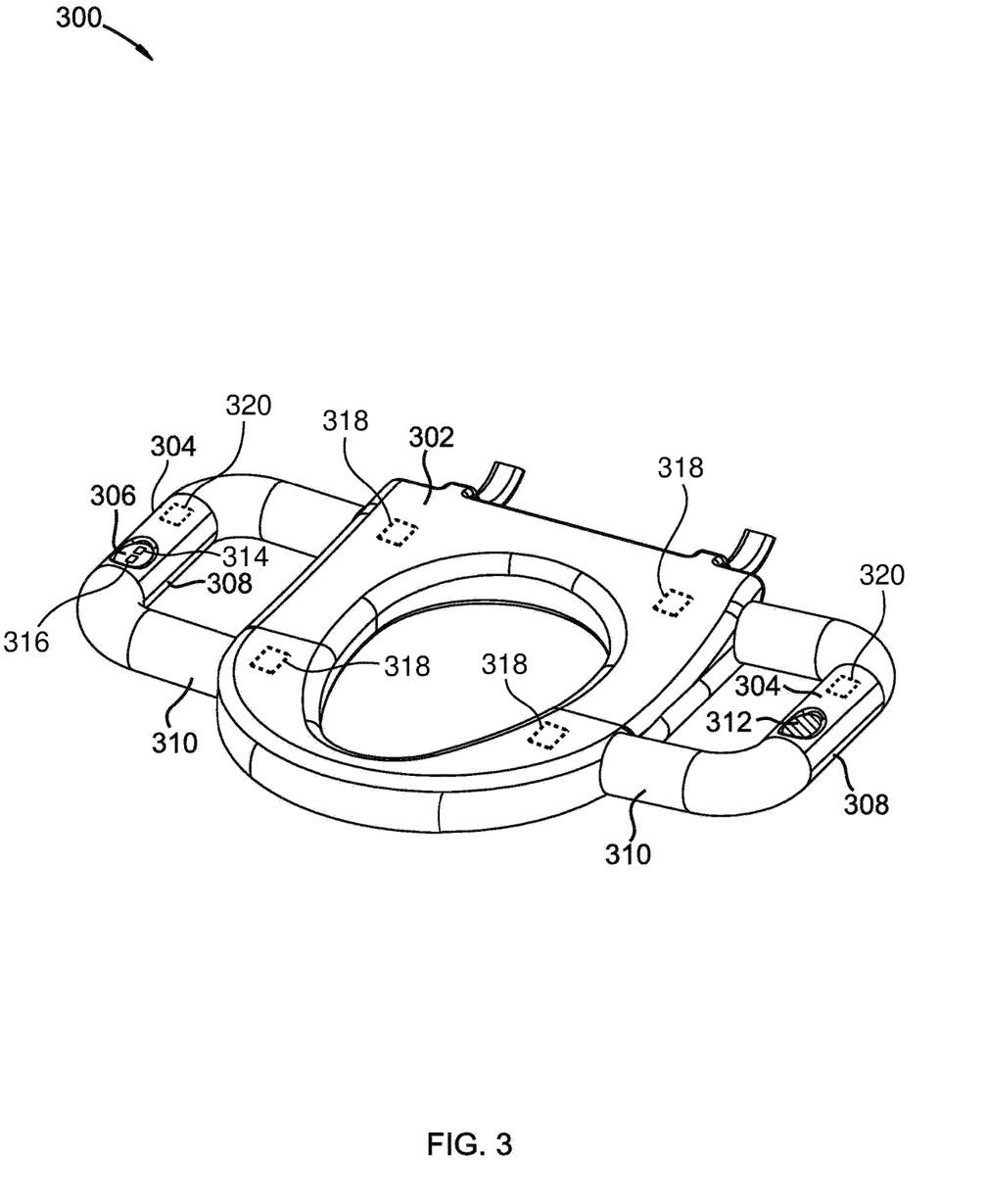
FIG. 3 depicts a perspective view of an instrumented toilet seat.

In some embodiments, handle 104 includes one or more pressure sensitive switches 320 (see FIG. 3). These switches 320 may be positioned such that, when a user places his or her hand on handle 104, light transmitters 110 and light receivers 510 actuate to take readings. When the user removes his or her hand from handle 104, light transmitters 110 and light receivers 510 cease transmitting and receiving, respectively. In embodiments where handle 104 further includes bioimpedance electrodes, the bioimpedance electrodes also activate and deactivate when the hand of the user is placed on or taken off handle 104, respectively.

In some embodiments, toilet seat 114 includes one or more pressure sensitive switches 318 (see FIG. 3). These switches 318 may be positioned such that, when a user places himself or herself on toilet seat 114, the light transmitters 314 (see FIG. 3) and light receivers 316 (see FIG. 3) actuate to take readings. When the user removes himself or herself from toilet seat 114, the light transmitters 314 and light receivers 316 cease transmitting and receiving. In embodiments where handle 104 further includes bioimpedance electrodes, the bioimpedance electrodes also activate and deactivate when the user places himself or herself on or removes himself or herself from toilet seat 114, respectively.

In some embodiments, apparatus 100 includes a speaker system which communicates information to a user. When a different positioning of a user's hand or fingers is needed for good readings, the speakers tell the user to reposition his or her hands as needed. Also, the speakers communicate blood oxygen saturation levels, heart rate, diastolic pressure, systolic pressure, etc. to the user.

For example, in some embodiments, a user is interested in whether or not his or her blood oxygen saturation levels have increased or decreased since his or her last time using toilet seat 114. The speaker system receives commands from a controller 102 each time he or she uses toilet seat 114, to inform him or her whether his or her blood oxygen saturation levels have changed or remained the same. Similarly, controller 102 contains instructions for recording previous heart rates, diastolic pressures, systolic pressures, etc. and using said information to compare subsequent data and report on the difference to the user. In some further embodiments, controller 102 includes instructions to compare biometric data obtained from a user for subsequent use, such as for toilet controls and for reporting change in heartrate, bioimpedance measurements, body temperature, blood oxygen saturation levels, diastolic pressure, systolic pressure, etc.

In some embodiments, apparatus 100 includes one or more microphones which receive information and commands from a user. The user may command that information be stored in memory within toilet seat 114. The user may also command that information be sent to his or her physician. In further embodiments, apparatus 100 also includes a speaker system. In such embodiments, the speaker system prompts a user for information regarding his or her health. The user's responses may be stored in memory and may be sent to his or her physician. The user may command toilet seat 114 to tell him or her his or her blood oxygen saturation levels, heart rate, diastolic pressure, systolic pressure, etc., and toilet seat 114 will communicate the corresponding information.

In some embodiments, apparatus 100 includes visual display 118. Visual display 118 communicates a user's blood oxygen saturation levels, heart rate, diastolic pressure, temperature, systolic pressure, etc. to the user. In some further embodiments, apparatus 100 also includes one or more microphones. A user is prompted by visual display 118 to answer one or more questions, which the user answers audibly or via another peripheral device such as a keyboard or smartphone. In some embodiments, visual display 118 is a touchscreen display.

In some embodiments, toilet seat 114 includes one or more force sensors. These force sensors determine weight distribution of a user. In conjunction with other data, data from the force sensors help determine the balance of the user.

In some embodiments, apparatus 100 includes one or more handles 104. Handles 104 include one or more force sensors. A user pulls up, pushes down, or pushes out handles 104 to assess his or her strength. This data is used by controller 102 to calculate strength of the user and his or her level of muscular atrophy, if any.

In some embodiments, apparatus 100 includes fiber optic cable 112 which transports light signals sent by light transmitters 110. For example, in some embodiments, apparatus 100 includes a single light transmitter 110. Fiber optic cable 112 receives signals from light transmitter 110 and transfers it to one or more light receivers 510.

FIG. 3 depicts a perspective view of an instrumented toilet seat. Apparatus 300 includes toilet seat 302. Toilet seat 302 includes handles 310. Handles 310 includes light transmitters 314 light receivers 316, top bioimpedance electrodes 304, bottom bioimpedance electrodes 308, transparent surface 306, and lenticular lens surface 312. Though not shown, toilet seat 302 includes a power source and a controller. The power source powers the controller, light transmitters 314, and light receivers 316. The controller includes instructions to record photoplethysmographical and bioimpedance data. The controller is coupled to the light receivers and/or light transmitters as well as the bioimpedance electrodes to measure and record data.

In some embodiments, handle 104 is retractable into toilet seat 114. After use, handle 104 retracts into toilet seat 114 and one or more of light transmitters 110 emit ultraviolet wavelength rays of light. The ultraviolet rays kill bacteria and partially sanitize handle 104. After a time period specified, which time period is dependent on surface area and geometry of handle 104, handle 104 extends out of toilet seat 114. In some further embodiments wherein apparatus 100 includes two or more handles 104, all of handles 104 may be retractable into toilet seat 114 and may be treated the same as described above for one handle 104. In some other further embodiments, wherein handle 104 and/or toilet seat 114 include(s) pressure sensitive switches, handle 104 retracts automatically after a user removes himself or herself from toilet seat 114, in response to either opening or closing one or more of the pressure sensitive switches. In some yet further embodiments, a user gives commands to a controller to retract handle 104 by any of a variety of means including a keypad, a visual touch screen display, microphones, a smartphone, etc.

Figure 2:
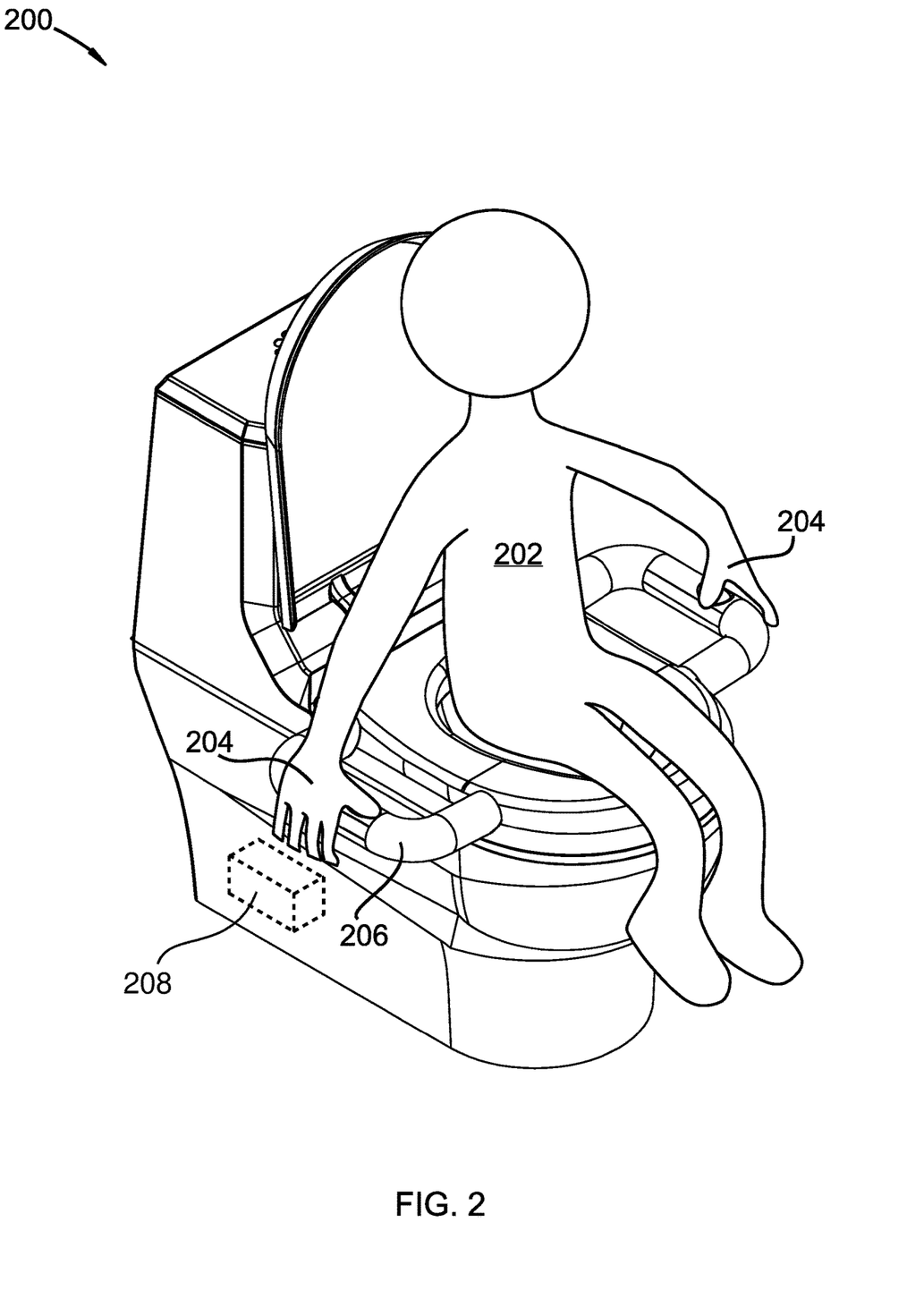
FIG. 2 depicts an embodiment similar to FIG. 1, further including a user.

FIG. 2 depicts an embodiment similar to FIG. 1, further including a user. Apparatus 200 includes a toilet seat comprising handles 206. As shown, user 202 places hands 204 on handles 206. Hands 204 of user 202 may be positioned such that light transmitters send light signals through hands 204, and light receivers collect any of the light signals which reflect off an interior layer of tissue of hands 204.

FIG. 3 depicts a perspective view of an instrumented toilet seat. Apparatus 300 includes toilet seat 302. Toilet seat 302 includes handles 310. Handles 310 includes light transmitters, light receivers, top bioimpedance electrodes 304, bottom bioimpedance electrodes 308, transparent surface 306, and lenticular lens surface 312. Though not shown, toilet seat 302 includes a power source and a controller. The power source powers the controller, light transmitters, and light receivers. The controller includes instructions to record photoplethysmographical and bioimpedance data. The controller is coupled to the light receivers and/or light transmitters as well as the bioimpedance electrodes to measure and record data.

Figure 4:
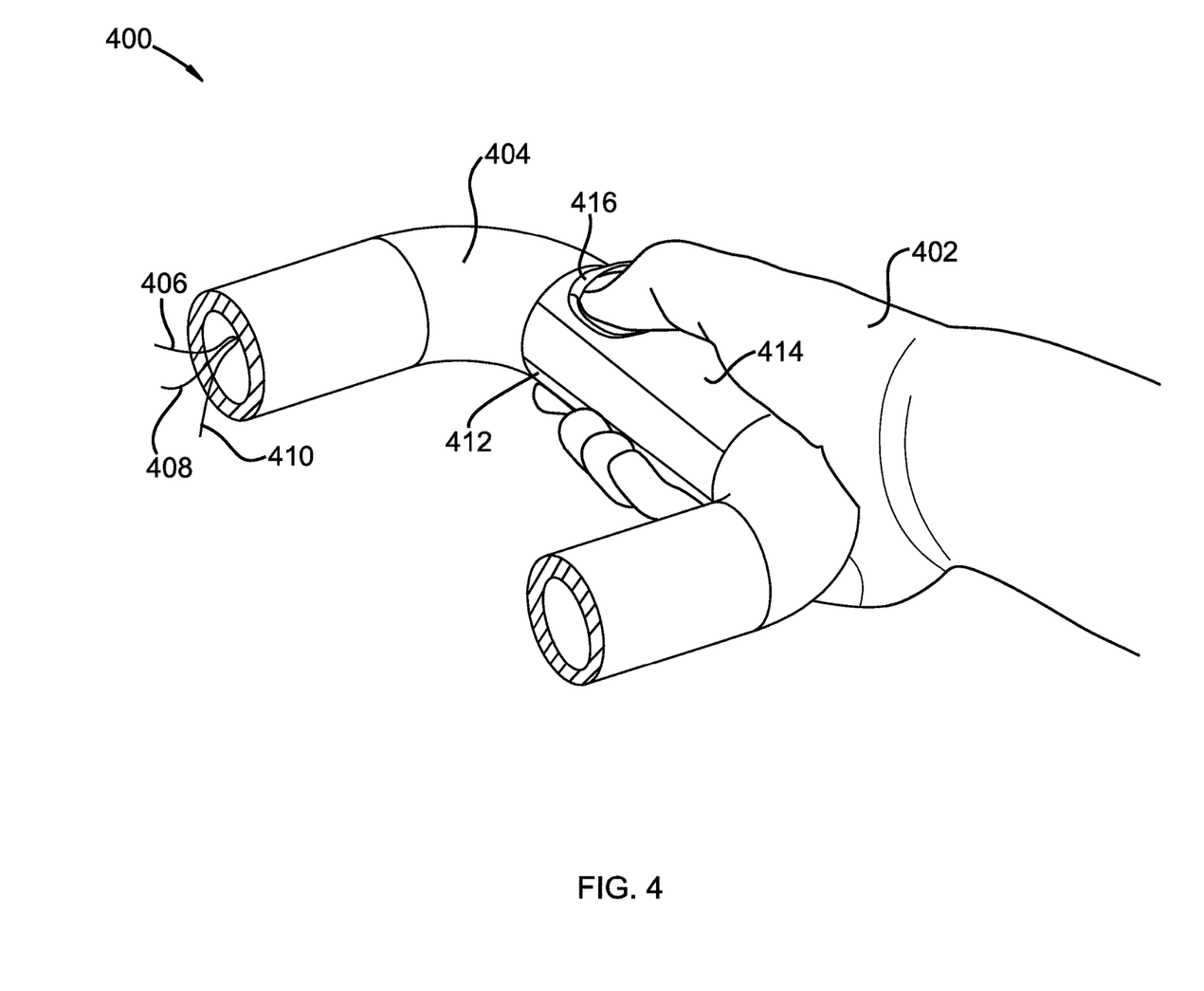
FIG. 4 depicts a perspective view of a handle with a thumb shield.

FIG. 4 depicts a perspective view of a handle with a thumb shield. Apparatus 400 includes handle 404. Handle 404 includes data wire 406, power wire 408, fiber optic cable 410, top bioimpedance electrode 414, bottom bioimpedance electrode 412, and thumb shield 416. Hand 402 of a user is placed such that a thumb of hand 402 is positioned under thumb shield 416 and pressed against a transparent surface. Underneath the transparent surface is a light transmitter (not shown) which emits light signals through the thumb of hand 402. The light signals may be partially absorbed by the blood and tissues of the thumb, but parts of the light signals which transmit through the thumb may be incident upon thumb shield 416. In some embodiments, thumb shield 416 contains one or more light receivers. In some other embodiments, thumb shield 416 is coupled to fiber optic cable 410, which transfers light signals incident on thumb shield 416 to a light receiver on the other end of fiber optic cable 410. For example, in some other further embodiments, apparatus 400 includes a toilet seat which includes a light receiver to which fiber optic cable 410 is coupled.

Data wire 406 transfers data from light transmitters, top bioimpedance electrode 414, bottom bioimpedance electrode 412, and/or light receivers to a controller included either in handle 400 or in a toilet seat. Power wire 408 transfers power from a power source to light transmitters, top bioimpedance electrode 414, bottom bioimpedance electrode 412, and/or light receivers. In some embodiments, data wire 406, power wire 408, and fiber optic cable 410 may be contained within a covering which facilitate motion. In these embodiments, handle 404 may move with the motion of hand 402.

FIG. 5 depicts a side view of a photoplethysmographical device. Apparatus 500 includes a spring-loaded hinge including top wing 504, bottom wing 520, and spring-loaded knuckle and pin assembly 506. Top wing 504 includes first light receiver 508 and second light receiver 510. Bottom wing 520 includes light transmitter 518. As shown, when finger 502, having finger nail 516, is placed between top wing 504 and bottom wing 520, spring-loaded knuckle and pin assembly 506 maintains a spring moment which forces top wing 504 and bottom wing 520 against finger 502 in opposite directions. This ensures that surfaces of finger 502 may be close to surfaces of top wing 504 and bottom wing 520. When light transmitter 518 is actuated, it emits light within a range of wavelengths which transmits through finger 502. Part of the emitted light which isn't absorbed or deflected by finger 502 is incident on first light receiver 508 or on second light receiver 510. The emitted light has different wavelengths as it passes through different parts of finger 502, as shown by first light ray 512 and second light ray 514. In addition, as second light ray 514 transmits through finger nail 516, some of its light is absorbed, while some of its light is reflected. Though not shown, apparatus 500 is attached to one or more handles included on a toilet seat.

Figure 6:
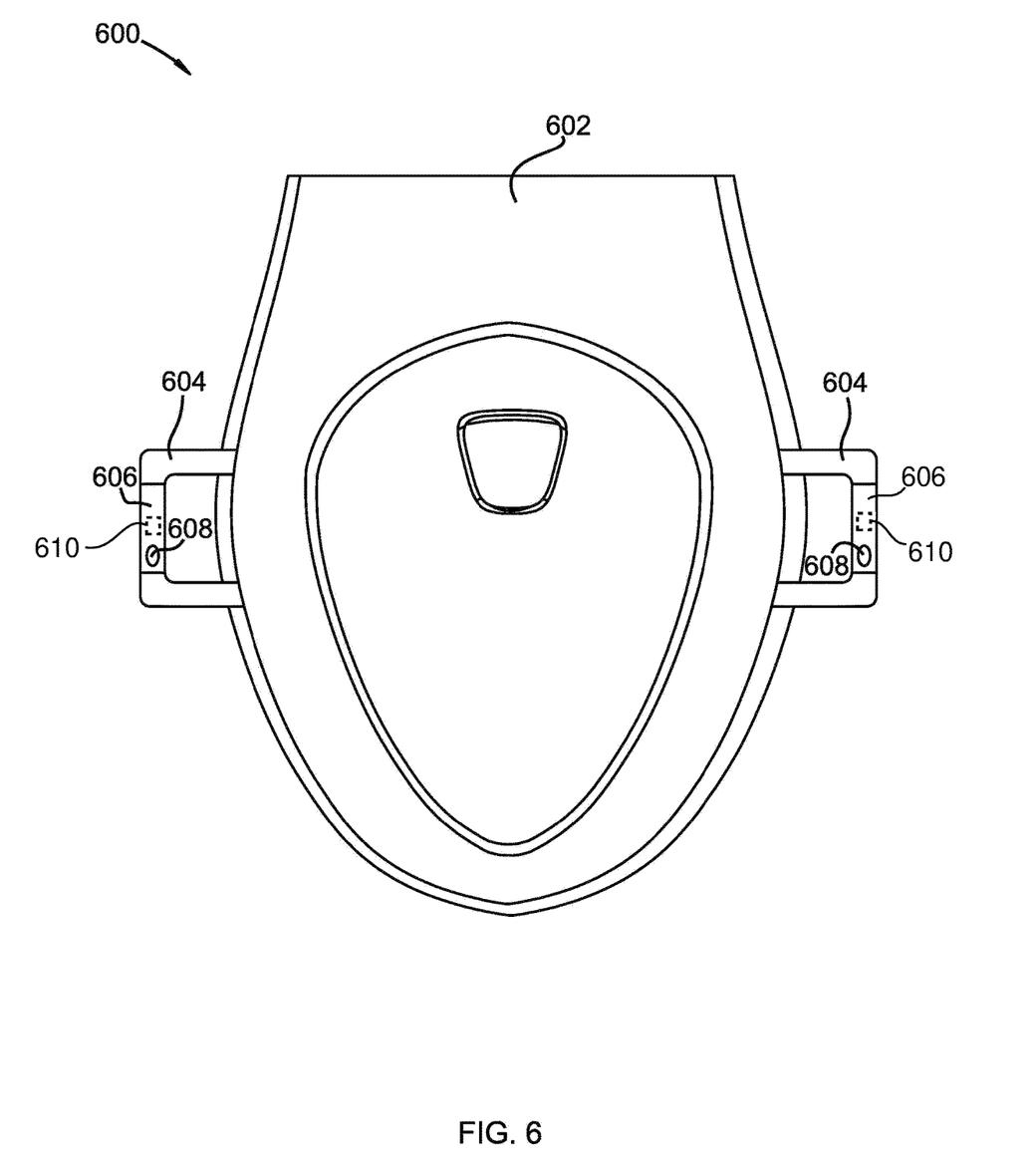
FIG. 6 depicts a top view of a toilet seat placed on a toilet.

FIG. 6 depicts a top view of a toilet seat placed on a toilet. Apparatus 600 includes toilet seat 602. Toilet seat 602 includes multiple handles 604. Handles 604 each include one or more photoplethysmograms 608 and one or more bioimpedance electrodes 606. Though not shown, apparatus 600 includes a controller and one or more speakers located inside toilet seat 602 and/or handles 604. When a user sits on toilet seat 602, he or she holds handles 604, positioning his or her fingers and palms on photoplethysmograms 608 and bioimpedance electrodes 606. Photoplethysmograms 608 and bioimpedance electrodes 606 communicate information about the user with the controller. The controller includes instructions to store information received from photoplethysmograms 608 and bioimpedance electrodes 606, to compare the information with previously stored information, to determine which user is sitting on the toilet seat based on the current and previously stored information, and to communicate to the user via the speakers the current information obtained from photoplethysmograms 608 and bioimpedance electrodes 606, and a comparison with the previously stored information.

Figure 7A:
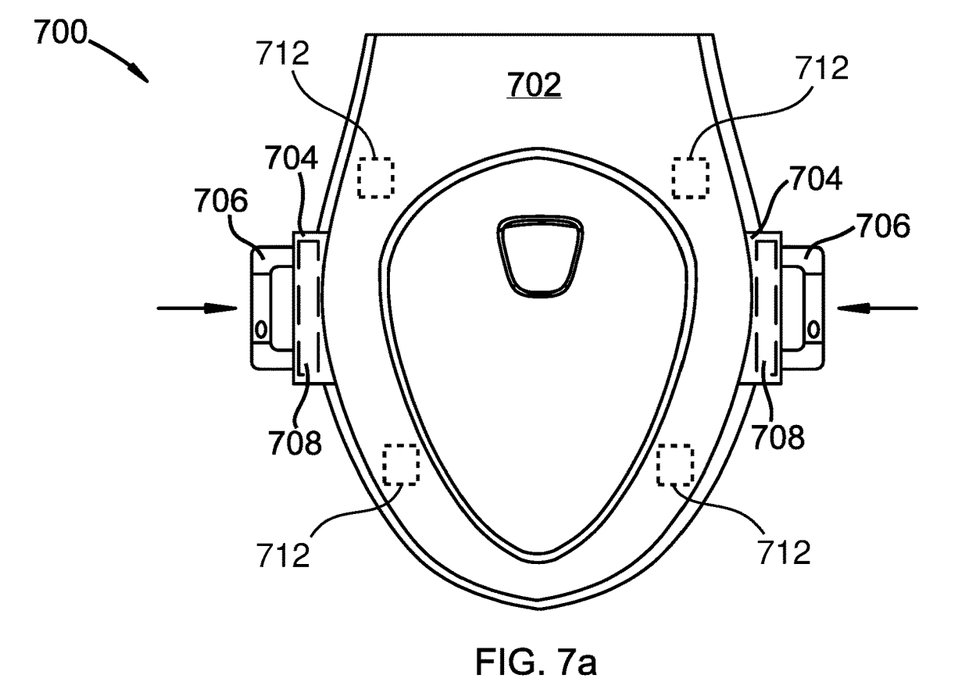
FIG. 7*a* and FIG. 7*b* depict a toilet seat with retractable handles.
Figure 7B:
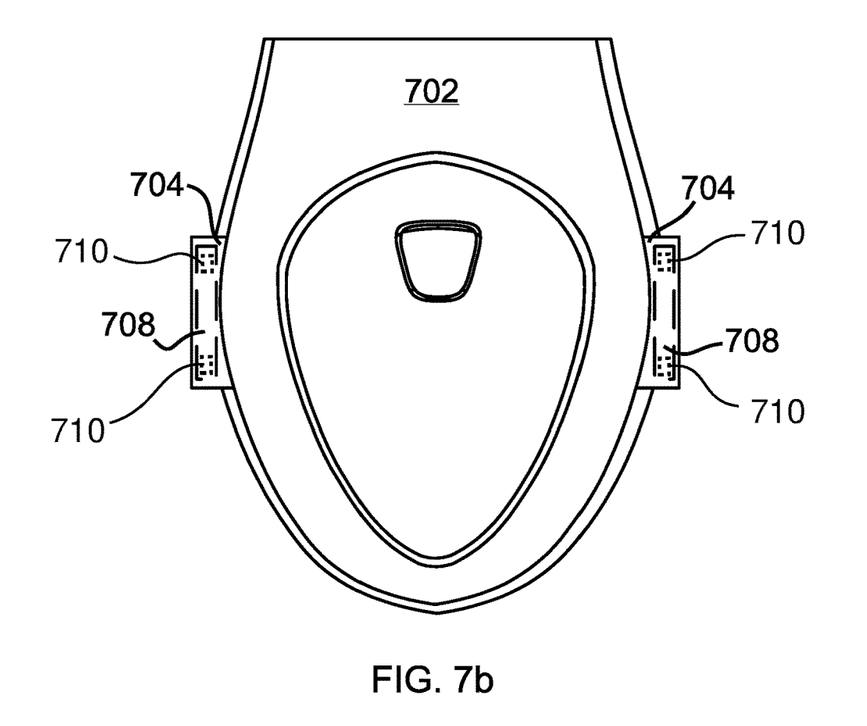

FIG. 7a and FIG. 7b depict a toilet seat with retractable handles. Apparatus 700 includes toilet seat 702. Toilet seat 702 includes retractable handles 706 and handle-receivers 704. Handle-receivers 704 include cavities 708. When a user is removed from toilet seat 702, handles 706 retract into cavities 708. Handles 706 may be sterilized by ultraviolet (UV) light sources 710, emitted either from handles 706 or from UV light emitters positioned within handle-receivers 704. In some embodiments, toilet seat 702 includes force sensors (not shown) and a controller 208 (see FIG. 2). When the user is removed from toilet seat 702, the force sensors 712 send data to the controller. The controller includes instructions to retract handles 706 for a specified period and activate the UV light emission. After the specified period, the controller sends electric signals to stop the UV light emission and extend handles 706 to their original position.

Figure 8:
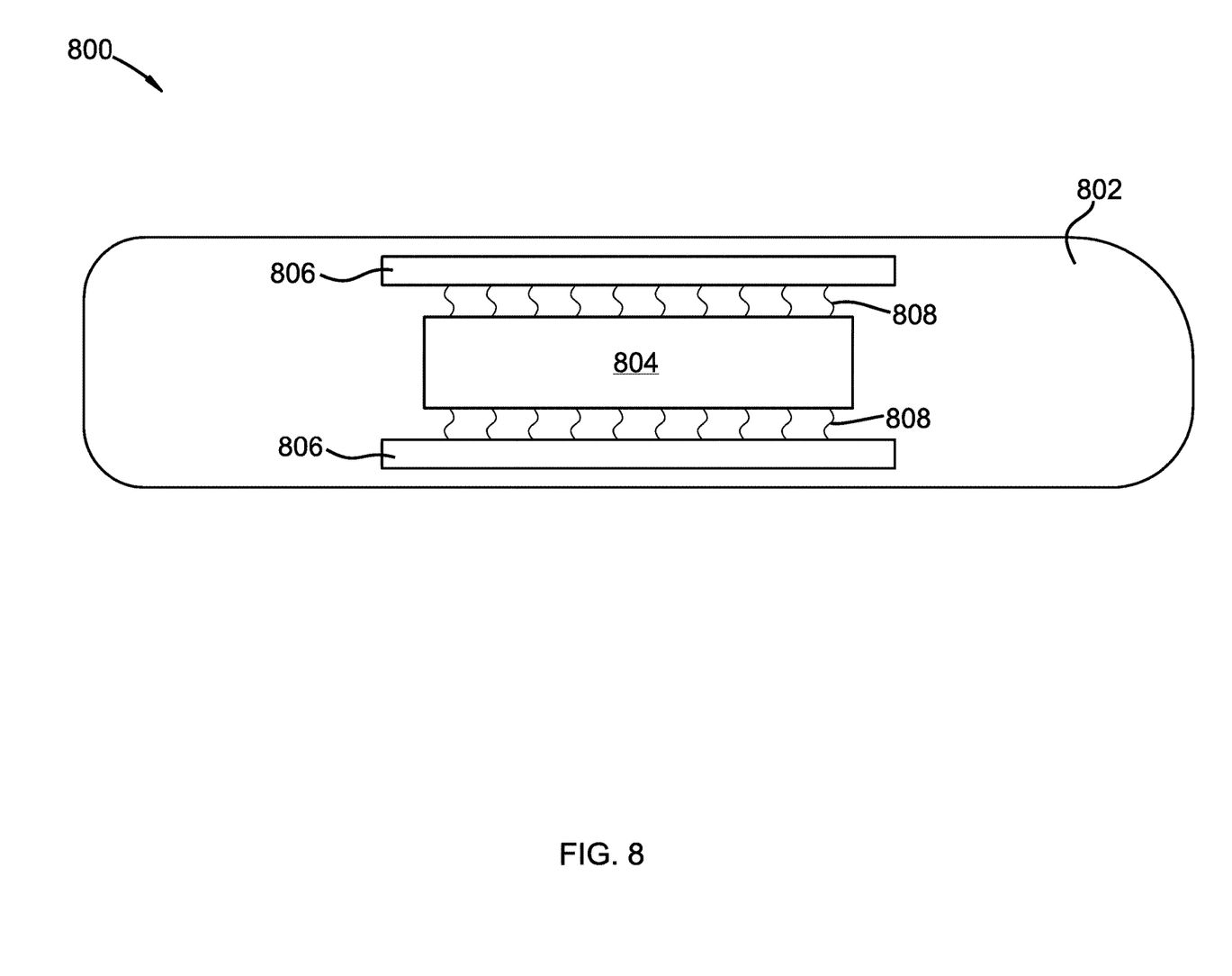
FIG. 8 depicts a ultrasound toilet seat handle.

FIG. 8 depicts an ultrasound toilet seat handle. Apparatus 800 includes handle 802. Handle 802 includes slot 804 and ultrasound transmitters and receivers 806. Slot 804 may be located on a bottom, side, or top of handle 802. A user may curl the ends of one or more fingers inside of slot 804 while holding handle 802. When a user places his or her hand or fingers into slot 804, ultrasound waves 808 may be transmitted through bones and tissues in a user's hand or fingers and/or reflected off various layers of tissues and bones in a user's hand or fingers in order to image bones and tissue. Quantitative ultrasound (QUS) may be used to detect bone density. Reflection and refraction of ultrasonic waves 808 may be used to image and determine density of bones and tissue. Backscattering and reflection methods may be used in combination with waves transmitted through a finger or hand to image bone, blood vessel, blood flow, and tissue in fingers or a hand of a user. Ultrasound waves 808 may transmit through and/or reflect off of bones in the hand, allowing bone mineral density to be determined as a function of wave propagation and/or reflected wave scattering. Reflected wave and transmitted wave attenuation may be used to image bone, blood vessel, blood flow, and tissue in fingers or a hand of a user. Ultrasound waves 808 may be received on a second side of slot 804. Based on sound speed of travel through the bones in the hand, bone mineral density may be estimated by a controller coupled to ultrasound transmitters and receivers 806. Transmitters and receivers 806 may be a combination of transmitters and receivers on each side 806. Reflected, backscattered, and transmitted waves may be received on each side 806. Transmitted waves 808 may be multi-frequency waves or pulses transmitted by transmitter 806 (on top) which interact with waves 808 transmitted by the other transmitter 806 (on the bottom) in a non-linear fashion to produce sum and difference waves capable of imaging bone, blood vessels, blood flow, and tissue in fingers or a hand of a user.

In some embodiments, ultrasound waves 808 may be transmitted on a first side of slot 804 and received on a second side of slot 804, then ultrasound waves 808 may be transmitted on a second side of slot 804 and received on a first side of slot 804. This alternating pattern continues, and the controller gathers data over a determined number of iterations. This is for the purpose of obtaining more data for better estimation.

Figure 9A:
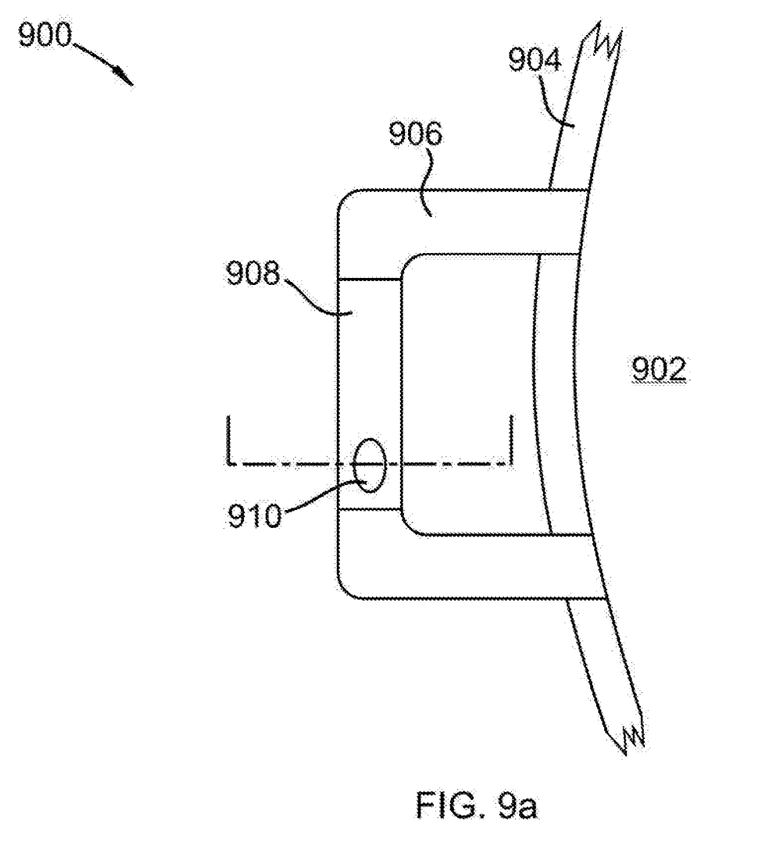
FIG. 9*a* and FIG. 9*b* depict a top view and a cross-sectional view of a grooved toilet seat handle with a photoplethysmogram, respectively.
Figure 9B:
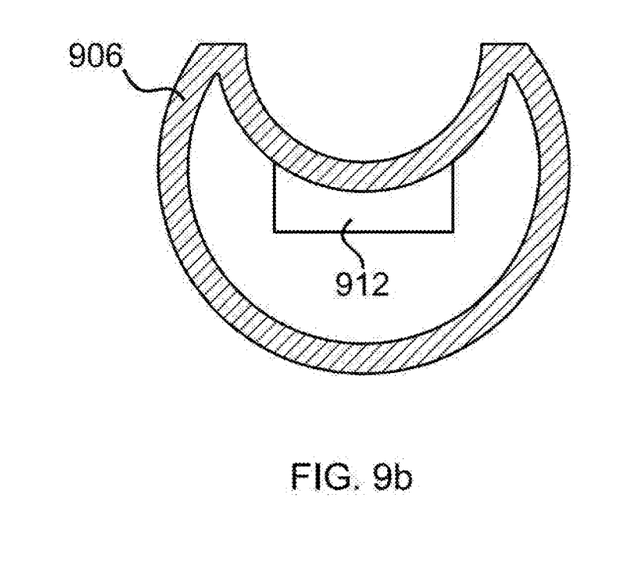

FIG. 9a and FIG. 9b depict a top view and a cross-sectional view of a grooved toilet seat handle with a photoplethysmogram, respectively. Apparatus 900 includes toilet seat 904. Toilet seat 904 includes one or more handles 906. Each of handles 906 include a grooved section 908, which grooved section 908 includes transparent section 910 and a photoplethysmogram 912 positioned at transparent section 910. When a user places a finger on transparent section 910, photoplethysmogram 912 uses reflection photoplethysmography (described above).

Figure 10:
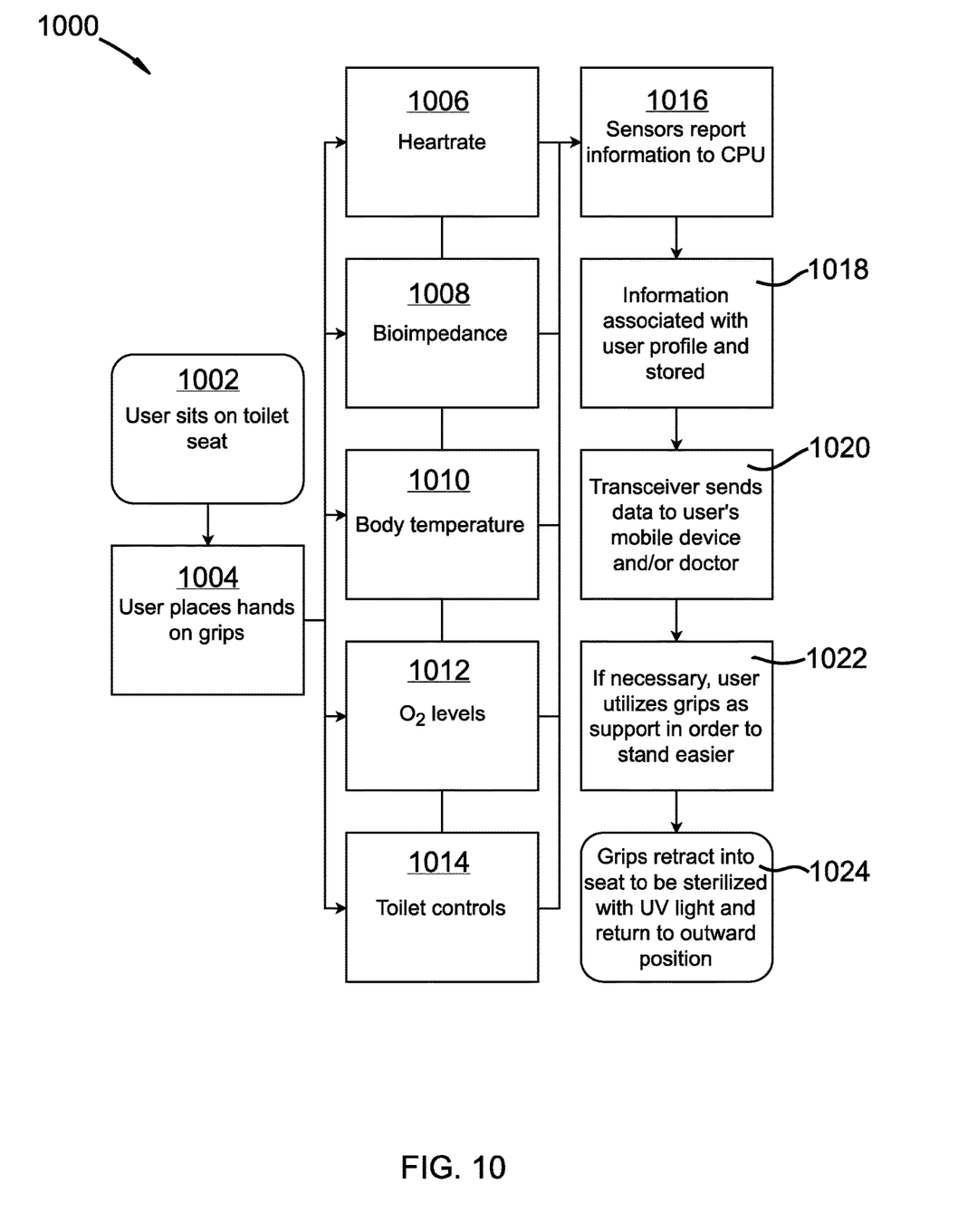
FIG. 10 depicts an embodiment of a method for obtaining biometrics using instrumented toilet seat handles.

FIG. 10 depicts an embodiment of a method for obtaining biometrics using instrumented toilet seat handles. Method 1000 includes block 1002. At block 1002, a user sits down on a toilet seat. The toilet seat includes handles. At block 1004 a user places his or her hands on the handles. Light transmitters, light receivers, and bioimpedance electrodes inside of the handles collect data. At block 1006 the light transmitters and light receivers use photoplethysmography to determine heart rate information. At block 1008 the bioimpedance electrodes collect bioimpedance measurements. In some embodiments, the handles include thermistors. At block 1010 the thermistors enable collection of body temperature data via a controller. At block 1012, the light transmitters and light receivers use photoplethysmography to determine blood oxygen saturation information. At block 1014, toilet controls may be determined based on biometric information and/or previously stored biometric information is utilized by a controller to automatically set toilet controls based on previous user preferences. For example, in some embodiments, the toilet seat includes heaters which have adjustable intensity and timer settings.

At block 1016, Light transmitters, light receivers, bioimpedance electrodes, and other sensors report information to the controller. At block 1018, the reported information is associated with a user profile and stored. In some embodiments, this is done automatically by creating profiles which may be distinguished solely by characteristic bioimpedance measurements. Each time a same user uses the toilet seat, a combination of bioimpedance information is similar if not exactly the same, and so a same user profile is used.

At block 1020, a transceiver coupled to the controller sends biometric information to a user's peripheral device and/or to his or her doctor's peripheral device. In some embodiments, the user's peripheral device is a mobile device, such as a smart phone, laptop, tablet, etc. At block 1022, if needed, the user uses the handles to support himself or herself in order to stand more easily. Otherwise, he or she simply stands. At block 1024, the handles retract into the toilet seat. The handles may be sterilized with ultraviolet (UV) light for a period of time. After the period of time has ended, the handles return to their outward position.

What is claimed is:

1. A toilet comprising:
   a bowl adapted to receive excreta;
   a seat having at least one extendable and retractable handle adapted for use as a support by a user;
   wherein the at least one handle further comprises at least one health sensor comprising at least one light transmitter and at least one light receiver; and
   wherein the at least one handle further comprises an ultrasonic sensor comprising:
      a slot adapted to receive at least a part of a user's hand;
      an ultrasonic transmitter; and
      an ultrasonic receiver, wherein the ultrasonic transmitter and the ultrasonic receiver are configured to image tissue in a user's hand; and
   a controller coupled to the at least one sensor adapted to operate the at least one sensor and process data from the at least one sensor; and
   the controller further coupled to the ultrasonic transmitter and the ultrasonic receiver to operate the ultrasonic transmitter and the ultrasonic receiver and process data from the ultrasonic transmitter and the ultrasonic receiver.

2. The toilet of claim 1 wherein the seat further comprises a slot for each of the at least one handle into which the handles may retract and at least one ultraviolet light source in each slot for sanitizing the handles.

3. The toilet of claim 1 wherein the at least one handle further comprises one or more pressure sensitive switches adapted to detect a user grasping the at least one handle.

4. The toilet of claim 1 wherein the at least one handle further comprises one or more inductive switches adapted to detect a user grasping the at least one handle.

5. The toilet of claim 1 wherein the at least one handle further comprises one or more capacitive switches adapted to detect a user grasping the at least one handle.

6. The toilet of claim 1 wherein the at least one handle comprises a cavity covered by a transparent material, wherein the at least one health sensor is positioned inside the cavity facing the transparent material.

7. The toilet of claim 1 wherein the at least one handle comprises at least one pressure sensitive switches.

8. The toilet of claim 1 wherein the at least one handle comprises at least one electrode for obtaining the user's bio-impedance or temperature.

9. The toilet of claim 1 wherein the seat comprises one or more pressure sensors adapted to detect a user on the seat.

10. The toilet of claim 1 wherein the seat comprises one or more force switches adapted to detect a user on the seat.

11. The toilet of claim 1 wherein the at least one light transmitter comprises at least one light emitting diode.

12. The toilet of claim 1 wherein the at least one light transmitter comprises at least one halogen light.

13. The toilet of claim 1 wherein the at least one light transmitter comprises at least one laser.

14. The toilet of claim 1 wherein the at least one light receiver comprises at least one capacitive coupled display.

15. The toilet of claim 1 wherein the at least one light receiver comprises at least one photodiode.

16. The toilet of claim 1 further comprising a visual display of information obtained from the at least one health sensor and the ultrasonic sensor.

17. The toilet of claim 1 wherein the at least one health sensor comprises at least one photoplethysmography sensor.

18. The toilet of claim 17 wherein the at least one photoplethysmography sensor emits light at wavelengths between visible and infrared spectrums.

* * * * *